United States Patent [19]
Ochoa et al.

[11] Patent Number: 5,266,301
[45] Date of Patent: Nov. 30, 1993

[54] METHOD FOR RAPID IN VIVO ASSESSMENT OF INTRAVENOUS IRRITATION OF PHARMACEUTICAL COMPOSITIONS

[75] Inventors: Ricardo Ochoa, Kalamazoo; Bruce C. Graves, Portage, both of Mich.

[73] Assignee: The Upjohn Company, Kalamazoo, Mich.

[21] Appl. No.: 717,607

[22] Filed: Jun. 20, 1991

Related U.S. Application Data

[63] Continuation-in-part of Ser. No. 581,716, Sep. 13, 1990, abandoned.

[51] Int. Cl.⁵ ............................................. G01N 33/15
[52] U.S. Cl. .......................................... 424/9; 128/630
[58] Field of Search ............................. 424/9; 128/630

[56] References Cited

PUBLICATIONS

Morita et al. "Intravenous Irritation Test of DI-63 in Rabbits" PreClin. Rep. 13(1) 1987 (Abstract).
Nomura et al. "Intravenous Irritation Test of Naftidrofuryl LS-121 LS-121 in Retroauricular Veins of Rabbits" PreClin. Rep. 11(2) 1985 Abstract.

*Primary Examiner*—Glennon H. Hollrah
*Assistant Examiner*—B. M. Burn
*Attorney, Agent, or Firm*—Bruce Stein

[57] ABSTRACT

The present invention is a method for rapid in vivo assessment of intravenous irritation of pharmaceutical compositions. The assessment of the vascular irritability of new pharmaceutical agents, vehicles and their pharmaceutical compositions has traditionally been limited to histological characterization of postinfusion damage. These studies utilized about 15 conscious animals and required about two weeks to complete. The method of the present invention in contrast utilizes fewer animals and can be completed in as short as only about 2–4 hr. In addition the direct observation is contemporaneous with the infusion and utilized a central vein.

19 Claims, 1 Drawing Sheet

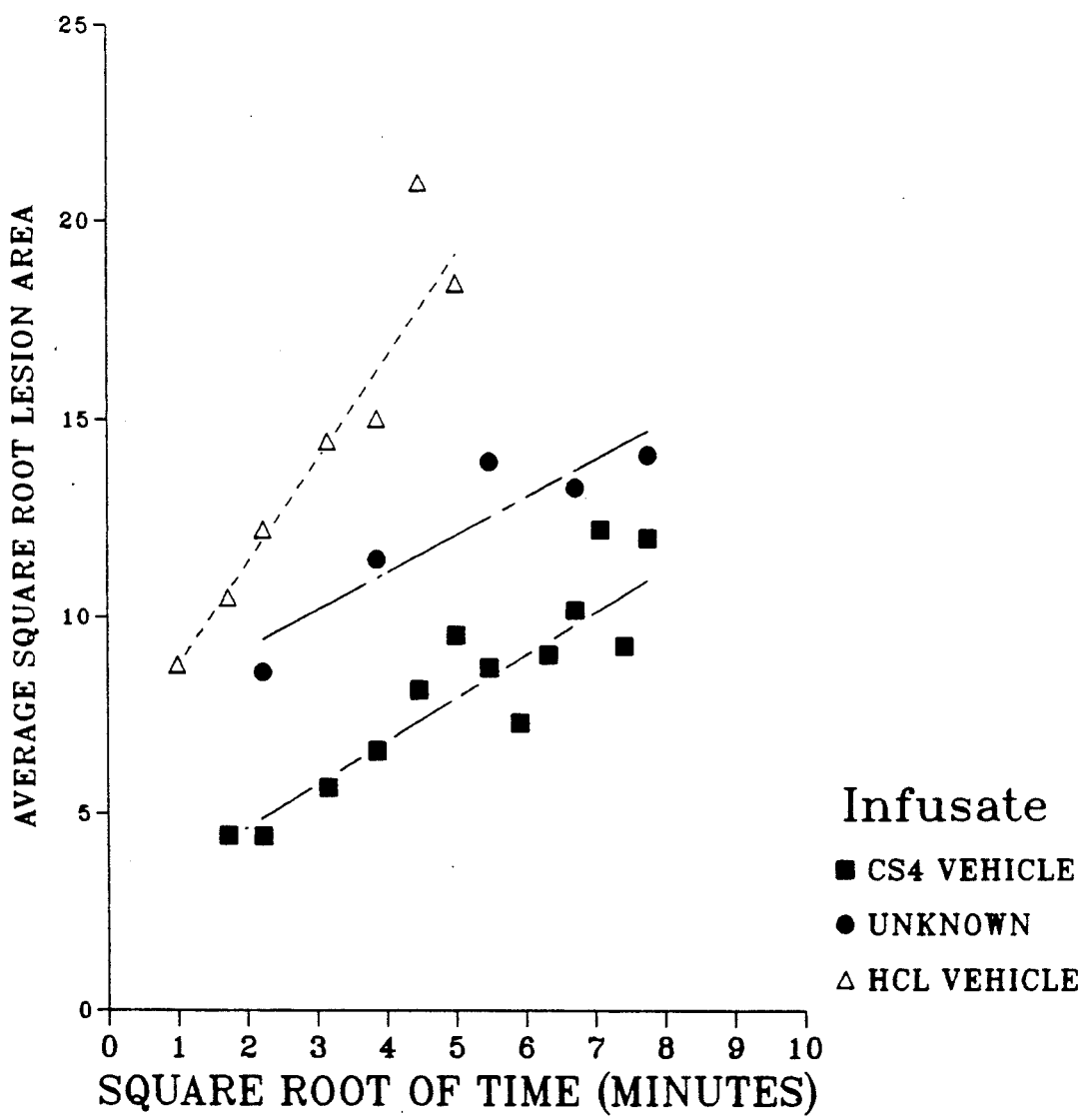

METHOD FOR RAPID IN VIVO ASSESSMENT OF INTRAVENOUS IRRITATION OF PHARMACEUTICAL COMPOSITIONS

CROSS-REFERENCE TO RELATED APPLICATIONS

The present patent application is a continuation-in-part of U.S. patent application Ser. No. 07/581,716, filed Sep. 9, 1990, now abandoned.

BACKGROUND OF THE INVENTION

1. Field of the Invention

The present invention is a method for rapid in vivo assessment of intravenous irritation of pharmaceutical compositions.

2. Description of the Related Art

The assessment of the vascular irritability of new pharmaceutical agents, vehicles and their pharmaceutical compositions has traditionally been limited to histological characterization of postinfusion damage. These studies utilized a number of conscious animals, about 15, and required about two weeks to complete. See, Japanese Journal of Antibiotics 39(12), 3353 (1986) using the vena retroauricularis of Japanese White rabbits and An. Esp. Pediatr. 11(1), 5 (1978) using the marginal ear vein of domestic rabbits.

The method of the present invention in contrast (1) utilizes fewer animals, (2) is performed on a central vein, (3) can be completed in as short as only about 2–4 hr and (4) provides for direct contemporaneous observation of results.

SUMMARY OF INVENTION

Disclosed is a method of assessment of intravenous irritation of an item selected from the group consisting of (A) a pharmaceutical agent, (B) a vehicle or (C) a pharmaceutical composition which comprises
  (1) immobilizing a small mammal and exposing a central vein,
  (2) insertion of a cannula into the central vein,
  (3) infusion of the item thru the cannula against the endothelial surface of the central vein,
  (4) direct observation of the damage produced by the item infused at the exposed area surrounding the end of the cannula, contemporaneous with the infusion.

BRIEF DESCRIPTION OF THE DRAWING

The drawing is a graph depicting the statistical comparison of the intravascular irritability (represented by the slope of the regression line depicted) of an unknown entity (pharmaceutical compound, etc.), shown as a solid circle, to a positive control (triangles), known to be a worse case, and to a more acceptable control (solid squares). The absolute position of each line is less important than the slope (steepness) since the slope represents the rate of lesion growth with time. The slope therefore is directly equated with the intravenous irritancy of the infused entity. A solution such as normal saline which is nonirritating has a slope of 0.

A square root of the transformation of the "TIME" and "LESION AREA" data linearizes the relationship between these two variables, which allows a statistical analysis of the slopes. Thus, The Y-axis is the Average Square Root of Lesion Area. Each point in the graph represents the mean of experiments. Standard error bars are not included for each point for clarity; however, they are taken into account in the statistical analysis and, therefore, are for all intents and purposes represented by the statistical results in the subtitle in the drawing.

The statistical comparison of slopes is done using 0.5 as the significance level. The unknown entity is compared first to the worse case positive control (hydrochloric acid vehicle), then to the more acceptable positive control (CS4, citric acid-sodium citrate buffer). These comparisons are listed in the subtitle as: UNKNOWN vs. hydrochloric acid vehicle (p=a), vs. CS4 (p=b). The value at "a" represents the p-value of the comparison between the unknown and the hydrochloric acid vehicle, whereas the value at "b" represents the p-value of the comparison between the UNKNOWN and CS4. P-values equal to or less than 0.05 suggest that there is a significant difference between the entities compared. When a new pharmaceutical agent is being analyzed it is preferred to conduct three experiments, the formulation vehicle alone, the new pharmaceutical agent in the formulation vehicle (pharmaceutical composition) and a reference standard and then compare the relative irritancy. Once a reference lesion development regression line (RLDRL) is established for the pharmaceutical composition, the reference formulation vehicle alone is infused to address its contributory effect on the irritancy of the pharmaceutical composition. The lesion development regression line obtained using only the formulation vehicle is then compared to that of the new pharmaceutical agent in the formulation vehicle (pharmaceutical composition) to determine if the new pharmaceutical agent, formulation vehicle, or both are primarily responsible for the irritancy of the reference formulation. A line, $Y = \alpha X + \beta$ represents the formation of the lesion with time and is used as a reference for assessing the vascular irritancy.

DETAILED DESCRIPTION OF THE INVENTION

The assessment of the vascular irritability of new pharmaceutical agents, their vehicles and/or new pharmaceutical delivery systems has traditionally been limited to the histological characterization of postinfusion damage. Though preregistration toxicity profiles of pharmaceutical agents may require definitive studies in vascular irritability such as those normally performed using the marginal ear vein of the rabbit, they may come late in the toxicity trials, consume numerous resources and often, if reformulation is recommended, delay Investigational New Drug (IND) filing. The discovery of novel membrane active compounds that modify and intervene in cellular systems will likely increase as science continues to unlock the secrets of functional cell biology. The membrane lipid interactions required of these new agents predict low solubilities in aqueous media. The specific nature of some compounds and the low pH required to keep them soluble in aqueous media may result in unacceptable blood vessel damage upon intravascular administration. The early assessment of the vascular irritability of new pharmaceutical agents and their vehicles provides important and timely information about a potential pharmaceutical agent and its formal toxic evaluation. This invention establishes a model to evaluate the vascular irritancy of intravenous formulations. The assessment by the process of the present invention is complete in less than 1 day and in most instances in less than 6 hr. Subjective results are obtained in about 1 hr with objective results in a few hours or a day or so.

A system has been developed using individual immobilized small mammals for the direct observation and quantification of the development of an endovascular lesions. It is preferred that the small mammal be selected from the group consisting of rodents, rabbits, guinea pigs and gerbils; it is more preferred that the small mammal be a rodent. The process of the present invention utilizes less than 10 animals, usually less than 5, in most cases less than 3 and can be performed on only 1 animal with reproducable results. However, stastically analysis requires more than one animal. The preferred rodent is a rat. Methods of immobilization include anesthetizing, decerebrating, tranquilizing and using curare; the preferred method is anesthetizing.

The small mammal is immobilized in the usual manner. The veins to be used are the central veins, not the peripheral veins as used by known methods. Suitable central veins include the posterior vena cava and the femoral vein. The preferred vein is the posterior vena cava (PVC). The central vein which is to be used is surgically exposed for insertion of the cannula as is known to those skilled in the art. If a ligature is placed around the PVC just anterior to the femoral bifurcation to discontinue blood flow to the lesion area during the fixation period, the tightening of the ligature causes dislocation of the cannula tip and associated thrombi form within the lesion area. Therefore, this technique is not preferred nor recommended. The beveled tip of a femoral infusion cannula (PREPARATION 1) is inserted and located against the ventral surface of the posterior vena cava; that is against the endothelial surface of the vein.

New vehicles, new drugs and/or new pharmaceutical compositions all can be analyzed utilizing the present invention. When analyzing a new pharmaceutical agent it is perferably to compare normal or physiological saline (0.9% sodium chloride), the vehicle to be used, the desired pharmaceutical composition and a solution of known irritability. Normal saline produces no lesions with the method of the present invention.

The solution to be infused should be infused at a rate of from about 5 to about 20 $\mu$l/min, more preferable from about 10 to about 12 $\mu$l/min for about 3 to about 60 min.

The amount and relative nature of intravenous irritation, or lack thereof, is determined by direct observation using photographs of the lesion forming at the cannula tip. Therefore, unlike other methods, the results are recorded and observed contemporaneous with the infusion. The photographs are obtained using a dissecting microscope during the course of the infusion. The infusion of the solution through the small cannula whose beveled tip is positioned against the endothelial surface of the PVC produces a lesion, if any, that is visually characterized by a clearing of the vessel wall. A compensating polar planimeter or other such apparatus is used to measure the total area of the lesion from photographs or video images taken at various time intervals. Time point measurements in the experiments over the period of the experiment are averaged and entered into a linear regression analysis. The data is statistically analyzed by standard linear regression methods known to those skilled in the art.

Further characterization of the standardized reference lesion is done using histological evaluation (transmission electron microscopy and light microscopy) along the damaged area of the PVC in tissues fixed after infusions of different durations. An understanding of the mechanisms causing the endothelial lesion is sought through histological evaluation. Fixed areas of the lesion produced by each of the infusates indicates general damage to the endothelium. The progressive increase in endothelial vacuolation toward the center of the lesion from the healthy margin as observed on light micrographs indicates concentration dependent damage to these cells. If electron micrographs show polymerized fibrin and the presence of red cell proteinaceous precipitates in the luminal area of the lesion this will confirm visual observations of the presence of a partitioned off area in which there is no mixing of blood with infusate. The exposure of endothelium to full strength infusate is typically seen when a slow infusion rate is used since a plenum along the luminal surface of the vessel is produced.

Electron micrographs of the lesion areas can reveal endothelial damage consisting of marked blebbing, precipitation of protein, margination of chromatin and sub-endothelial edema.

The present invention is a reproducible model to discriminate between the vascular irritability of intravenous infusates and those of a reference formulation known to produce reproducable vascular damage. The methodology described is sensitive enough to be used in the documentation of differences in irritability of formulations that have demonstrated both success and failure in animal safety studies.

The invention successfully distinguish the vascular irritability of intravenous infusates with respect to a reference formulation known to produce complications in animal safety studies.

The process of this invention can be effectively used to predict the success of newly developed pharmaceutical compounds and their formulations (pharmaceutical compositions) in animal toxicological studies and human use. The early assessment of vascular irritability will significantly contribute to shorten the decision making process between several potential pharmaceutical agents, pharmaceutical vehicles and/or particular pharmaceutical formulations and ultimately decrease the time necessary for Investigational New Drug (IND) submissions.

DEFINITIONS AND CONVENTIONS

The definitions and explanations below are for the terms as used throughout this entire document including both the specification and the claims.

DEFINITIONS

All temperatures are in degrees Centigrade.

PVC refers to posterior vena cava.

RLDRL refers to reference lesion development regression line.

Cannula refers to and includes any tube which delivers a liquid to a designated place and includes items such as catheters and needles.

Normal or physiocological saline refers to a 0.9% aqueous sodium chloride solution.

Alcohol refers to ethyl alcohol.

Pharmaceutically acceptable refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability.

When solvent pairs are used, the ratios of solvents used are volume/volume (v/v).

When the solubility of a solid in a solvent is used the ratio of the solid to the solvent is weight/volume (wt/v).

EXAMPLES

Without further elaboration, it is believed that one skilled in the art can, using the preceding description, practice the present invention to its fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

PREPARATION 1

Cannula Construction and Preparation

The femoral cannulas are made by gently heating polyethylene tubing (1.9 mm OD/1.04 mm ID) over a small alcohol burner until the plastic could be stretched to form a tube with a smaller lumen. One flared end is retained on the stretched small tubing to be used as a cone type connector. The other end of the small tube is cut at a bevel halfway between the points where it flared to the original larger tube. In order to insure consistency in the cannulas several pieces of tubing are pulled to an arbitrary length. Cross sections are then cut from each cannula and screened for similar internal diameter under a dissecting microscope. Based on this screen each cannula is selected and is labeled. A group of five cannula cross sections are then photographed in order to document their consistency. Each cannula is used for several experiments. The cannula number is noted for each experiment. Each cannula is dipped in a heparin complex agent (Heparin Complex 2%) and dried prior to use. This treatment is necessary to decrease the probability that thrombi would attach to the tip and indiscriminately change the flow pattern of the infusate leaving the cannula.

EXAMPLE 1

Infusion of Test Solution into Posterior Vena Cava of a Rat

Immobilization

Rats (180–350 g) are individually given intraperitoneal injections of 5-allyl-5-(2-cyclopenten-1-yl)barbituric acid, sodium salt (62.5 mg/ml, 2 $\mu$l/g body wt.) in order to achieve a surgical plane of anesthesia. Each animal is shaved in the abdominal area, left inside thigh area and the ventral neck area. After being placed on a heated surgery table the right jugular vein is cannulated and saline (approximately 10 $\mu$l/minute) is infused throughout each experiment to compensate for evaporative dehydration. A ventral incision is made from just below the ribs along the abdominal midline to a point approximately 1 cm cranial to the pubis. Lateral transsectional cuts are made on either side of the distal end of the midline incision. Modified safety pins are used to retract the edges of the skin and abdominal wall to expose the abdominal organs. The intact viscera are carefully lifted out of the abdomen and gently draped over the left retracted abdominal wall. A tissue paper covering is placed around the viscera and coated with warmed mineral oil. The abdominal cavity is then filled with warm mineral oil in order to minimize evaporative cooling and to improve optical clarity. The posterior vena cava is surgically cleared of overlying fat in order to obtain a clear view of the vein at a level approximately 2 cm posterior to the diaphragm. A fiber optic illuminator is used for incidental illumination of the area around the PVC.

Insertion of Cannula into Vascular System

The left hind foot is secured with tape prior to making a 1.5 cm incision along the inner thigh. The exposed femoral vein is then separated from the femoral artery by dissection for a length of approximately 0.5 cm. A 5 cm length of surgical silk (0 or finer) is passed under the exposed femoral vein and secured to the table using tape. A small incision is made in the femoral vein and the beveled femoral cannula (PREPARATION 1, approximately 0.5 mm in diameter) is inserted in a cranial direction. The cannula is fed into the vein until the tip is visible using a dissecting microscope at the chosen observation site within the posterior vena cava. By careful rotation the cannula tip is positioned with the beveled tip in clear view against the ventral luminal surface of the PVC, against the endothelial surface. The cannula is then secured with tape at the femoral site and the site is covered with oil saturated tissue paper.

Infusion

The infusions of reference formulation, whether pharmaceutical agent, vehicle or pharmaceutical composition, into the femoral vein are controlled by a Razel syringe pump using a 1/24 motor and 10 cc disposable syringe. This system delivers infusate at a calibrated rate of 12.2 $\mu$l/min. A second pump with the same configuration is used to infuse saline through the femoral cannula prior to starting the test or reference infusate. The time required for the cannula to fill is measured and permits an accurate determination of the time when the endothelium is first exposed to test infusate.

Evaluation

The lesions generated in the PVC are quantified using a compensating polar planimeter. The perimeter of the lesions are traced on photocopies of photographic enlargements taken at predetermined times. The resulting area measurements are expressed in vernier units.

The data are analyzed by group means and standard deviations of lesion measurements for each time point are calculated using a computer spread sheet. In cases where only one measurement is made in the group for a time point that value is reported. In all other cases, the mean measurement at each time point is reported for each group. A regression line is determined for the reference lesion development as well as for each comparative group data sets. The individual data obtained from measuring the lesion produced by the reference formulation are plotted against their respective time points. The calculated linear regression line for these data is superimposed on the data plot. The linear regression lines calculated for each of the comparative groups are individually plotted on separate graphs with the reference lesion line. The reference lesion development regression line (RLDRL) becomes the reference to which the three other groups are compared.

A simplified statistical interpretation is made when comparing the test article formulation lesion development lines to the RLDRL consists of visually comparing plots of the respective data sets to determine the degree of overlap in their associated standard errors. If there is no overlap of the standard error bars the slopes of the lines are considered significantly different.

The histopathology is determined by taking the PVC of one animal in each group and fixing it for histological examination by infusing Karnovsky's fixative [J. Cell Biol., 27, 137A (1965)] into the vein at the same rate as that of the reference or test infusate. Fixative is also dripped onto the posterior vena cava and filled into the abdominal cavity immediately after the beginning of the fixation infusion. In each case the posterior vena cava is cut transversely into small segments at three locations along the lesion. A section is taken at the proximal and distal ends of the lesion as well as in the middle of the affected area for histological comparison. Complete cross-sections of the PVC are taken from the segments for light microscopy and includes normal as well as damaged tissue. Additional segments are cut at the same locations and are trimmed for electron microscopic evaluation. The sections trimmed for electron microscopic evaluation included areas of normal tissue, the margin of the lesion and damaged endothelium.

We claim:

1. A method of assessment of intravenous irritation of an item selected from the group consisting of (A) a pharmaceutical agent, (B) a vehicle or (C) a pharmaceutical composition which comprises
   (1) immobilizing a small mammal and exposing a central vein,
   (2) insertion of a cannula into the central vein,
   (3) infusion of the item thru the cannula against the endothelial surface of the central vein,
   (4) direct observation of the damage produced by the item infused at the exposed area surrounding the end of the cannula, contemporaneous with the infusion.

2. A method of assessment of intravenous irritation of an item according to claim 1 where the item is a pharmaceutical agent.

3. A method of assessment of intravenous irritation of an item according to claim 1 where the item is a vehicle.

4. A method of assessment of intravenous irritation of an item according to claim 1 where the item is a pharmaceutical composition.

5. A method of assessment of intravenous irritation of an item according to claim 1 where the pharmaceutical composition is a solution.

6. A method of assessment of intravenous irritation of an item according to claim 1 where the small mammal is selected from the group consisting of rodents, rabbits, guinea pigs and gerbils.

7. A method of assessment of intravenous irritation of an item according to claim 6 where the small mammal is a rodent.

8. A method of assessment of intravenous irritation of an item according to claim 1 where the central vein is a posterior vena cava.

9. A method of assessment of intravenous irritation of an item according to claim 1 where immobilizing is selected from the group consisting of anesthetizing, decerebrating, tranquilizing or curarizing.

10. A method of assessment of intravenous irritation of an item according to claim 9 where immobilizing is anesthetizing.

11. A method of assessment of intravenous irritation of an item according to claim 1 where the observation is direct observation.

12. A method of assessment of intravenous irritation of an item according to claim 1 where the observation is made by use of a dissecting microscope.

13. A method of assessment of intravenous irritation of an item according to claim 1 where the observation is measuring the area of lesions.

14. A method of assessment of intravenous irritation of an item according to claim 1 where the assessment is completed in less than 1 day.

15. A method of assessment of intravenous irritation of an item according to claim 1 where the testing is completed in less than 6 hr.

16. A method of assessment of intravenous irritation of an item according to claim 1 where the assessment uses less than 10 animals.

17. A method of assessment of intravenous irritation of an item according to claim 1 where the assessment uses less than 5 animals.

18. A method of assessment of intravenous irritation of an item according to claim 1 where the assessment uses less than 3 animals.

19. A method of assessment of intravenous irritation of an item according to claim 1 where the assessment uses 1 animal.

* * * * *